United States Patent [19]

Repperger et al.

[11] Patent Number: 4,619,506

[45] Date of Patent: Oct. 28, 1986

[54] RANDOM PATTERN TRACKING ACCELERATION TOLERANCE TESTER

[75] Inventors: Daniel W. Repperger, Vandalia; Thomas J. Jennings, Dayton; David A. Ratino, Centerville, all of Ohio

[73] Assignee: The United States of America as represented by the Secretary of the Air Force, Washington, D.C.

[21] Appl. No.: 645,390

[22] Filed: Aug. 29, 1984

[51] Int. Cl.[4] ............................................. A61B 3/02
[52] U.S. Cl. ...................................... 351/243; 351/224
[58] Field of Search ............... 351/243, 244, 224, 225, 351/226

[56] References Cited

U.S. PATENT DOCUMENTS

| 2,316,042 | 4/1943 | Beitel, Jr. | 88/20 |
|---|---|---|---|
| 3,705,003 | 12/1972 | Lynn et al. | 351/39 |
| 4,169,592 | 10/1979 | Hall | 273/1 E |
| 4,255,022 | 3/1981 | Kuether et al. | 351/24 |
| 4,421,393 | 12/1983 | Cohen | 351/224 |

OTHER PUBLICATIONS

T. B. Sheridan and W. R. Farrell, Man-Machine Systems, 1974, MIT Press.

*Primary Examiner*—Rodney B. Bovernick
*Assistant Examiner*—P. M. Dzierzynski
*Attorney, Agent, or Firm*—Donald J. Singer; Gerald B. Hollins

[57] ABSTRACT

A G force acceleration effects monitoring apparatus involving a pair of LED or other visual stimulus arrays, one randomly patterned by an electronic driving apparatus and one patterned by the manipulation of a G force test subject. The electronic driving apparatus preferably includes a sum of sines algorithm and the test subject manipulations are received preferably from a joystick controller. Mounting of the apparatus in a centrifuge gondola and also in off-line training stations and use of the invention by animals are also disclosed.

23 Claims, 5 Drawing Figures

RANDOM PATTERN TRACKING ACCELERATION TOLERANCE TESTER

RIGHTS OF THE GOVERNMENT

The invention described herein may be manufactured and used by or for the Government of the U.S. for all governmental purposes without the payment of any royalty.

BACKGROUND OF THE INVENTION

This invention relates to the field of G force acceleration effect sensing accomplished by way of visual field and psychomotor tracking performance evaluation in a test subject.

When a human subject is exposed to increasing G force acceleration, a well-established sequence of degradation changes in the subject's blood circulation occur. In modern high-performance aircraft and spacecraft, these hemodynamic changes require consideration in order that a human operator remain physically able to function as an aircraft pilot or as a performer of technical functions. The change in human blood circulation is particularly severe in the case of +GZ axis G forces, forces directed downward from the head and tending to collect blood in the lower extremities of a subject's torso so that the blood supply to the brain and eye retina are diminished. Another severe condition results from −GZ axis acceleration forces which tend to collect excessive blood quantity and pressure in the brain and produce a red-out response. Supplemental body pressure apparatus and test subject physical "exercises" which tend to increase the tolerance of acceleration forces have been used in military equipment for some time; the G-suit is a well-known example of such apparatus and is particularly effective for increasing the tolerance of +GZ axis forces. G force acceleration in the other coordinate directions, that is, along the X axis, tending to press a test subject more firmly against a seat back or along the +Y axis, tending to move the subject to his left, are also detrimental to blood circulation to lesser degrees.

The progressive reduction of blood circulation particularly in response to increasing GZ forces results in several correspondingly progressive physiological effects, including a dimming of the subject's vision or "gray-out", a narrowing of the subject's visual field or vision tunneling, a total loss of vision or "blackout" and ultimately a loss of consciousness.

As a result of differences between the intra-ocular pressure and intracranial pressure in a human body, blood circulation to the eye is diminished prior to circulation to the brain, and a loss of vision, particularly far peripheral vision, generally precedes loss of consciousness in a G force test subject. This established order of circulatory disruption therefore provides a convenient and repeatable means by which a test subject's response to G forces can be objectively evaluated and by which the onset of undesirable effects in a test subject can be detected.

Exposure to G force acceleration is also known to degrade a test subject's psychomotor tracking performance in addition to the above-described circulatory or hemodynamic effects. The ability of a test subject to perform a task requiring both visual and psychomotor capabilities is therefore a doubly useful tool in assessing the degree of tolerance the subject exhibits to acceleration G forces. The combination of visual and psychomotor capability can therefore be desirably evaluated in a G force test environment by assigning a test subject to perform tasks which involve visual input and motion output; preferably the expected performance should allow measuring both the extent and the rate of degradation in the subject's visual field and psychomotor tracking ability.

Arrangements for combining a measurement of a test subject's visual field and psychomotor tracking ability under the influence of acceleration G forces are known in the art as is evidenced, for example, by the patent of Malcolm Cohen, U.S. Pat. No. 4,421,393 and the several G force effect measuring systems therein described.

The Cohen invention concerns a visual field perimeter and psychomotor tracking performance measuring apparatus for use with a human test subject centrifuge operated by the U.S. Navy. In the Cohen invention a semicircular array of light emitting diodes (LEDs) is arranged to subtend the lateral field of view of the test subject and is excited such that pairs of opposed diodes symmetrically located about a central viewing axis are sequentially illuminated at a programmed rate and in an inward or outward progressing sequence. The test subject in the Cohen apparatus employs a control stick to generate a nulling signal that maintains a desired peripheral field pair of light emitting diodes illuminated. The Cohen apparatus relies upon the test subject performing a manipulation of the control stick in response to peripheral vision diminishing with increased acceleration forces. The Cohen apparatus also contemplates the use of a pseudo-random pattern of LED excitation without, however, specifying the precise nature of the random signal or indicating how it is generated.

A conceptual advantage of the present invention over the Cohen apparatus concerns the achieved reduction in the ability of a test subject to bravado, enhance or cheat the measurement system by artificially indicating a better response to the G force effects than he actually experiences. In the present invention, the test subject is required to see the position of the driving visual stimulus in order to position a responding visual stimulus properly. In the absence of seeing the driving visual stimulus, the test subject is precluded from making any response and thus from enhancing his measured tolerance of the G force.

The Cohen patent also describes several prior art visual testing arrangements including one in which a lamp located in the test subject's visual periphery is randomly illuminated and the test subject is required to immediately press a button to extinguish the lamp. As indicated in the Cohen patent, this arrangement does not test the subject's visual field and the rate at which it collapses, nor does it measure the psychomotor tracking ability of the subject.

Additional distinctions of the present invention over the Cohen apparatus concern arrangement of the display in the present invention, including the two arrays of visual stimulus elements and the circuitry used for driving display LED elements.

Another example of prior patent art relating somewhat to the present invention is found in the patent of C.L. Kuether et al, U.S. Pat. No. 4,255,022, concerning an improved "perimeter" apparatus of the type used for vision testing in a medical examination environment. In the Kuether invention microprocessor techniques are employed to improve an existing perimeter device through incorporation of an electronically-controlled silent shutter and an electronically controlled operator lead-through system. The Kuether apparatus is of course unconcerned with testing for the effects of G force acceleration.

An example of prior art apparatus requiring the cooperation of a subject with a visual stimulus-generating machine is found in the patent of David J. Hall, U.S. Pat. No. 4,169,592 wherein there is described an electronic reflex challenging game requiring a player to respond to a randomly actuated one of three possible light bulbs within an increasingly shortened response time. The Hall apparatus is unconcerned with the player's physical environment and additionally involves only a race against time as the physical trait to be measured in the test subject.

Another example of prior patents concerning visual testing is found in the patent of J. R. Lynn et al, U.S. Pat. No. 3,705,003 n which a test subject operates a joystick control in response to an unpredictable or random sequence visual stimulus display in order to achieve mapping of his vision capability. The Lynn apparatus teaches the use of a cathode ray tube display which is arranged in a 64×64 or higher resolution grid and employs a four-bit intensity determining word at each grid location. As indicated at column 10, line 34 in the Lynn patent, the test subject is expected to move the joystick control in the general direction of the bright spot he has observed on the cathode ray tube screen. The Lynn apparatus defines a measurement tool called an error sector and determines if the test subject's response comes within an allowable number of error sectors of the cathode ray tube displayed spot.

The Lynn apparatus is of course intended for use in a medical testing environment in contrast with applicant's environment of acceleration G force effect testing; the Lynn apparatus moreover is silent with respect to providing feedback to the test subject as to the results of his joystick control manipulation. The Lynn apparatus also appears to depend on human operator generation of the random data used for test spot location.

Another example of prior art peripheral vision testing apparatus is found in the patent of R. J. Beitel, Jr. U.S. Pat. No. 2,316,042 which discloses an adjustable perimeter testing device used for medical vision testing and employing manually movable mechanical target or visual stimulus member. The Beitel apparatus includes the familiar perimeter screen and moving target concept, and further contemplates the use of multicolored targets. The Beitel apparatus is also intended for use outside the G force acceleration testing environment and employs manual positioning of the visual stimuli.

SUMMARY OF THE INVENTION

An object of the present invention is to provide a G force effect measuring apparatus which produces a true indication of the test subject's physical condition.

Another object of the invention is to provide a G force effect sensing apparatus which can be arranged to train a test subject using an off-line, low-cost preliminary environment prior to stress phase G force testing.

Another object of the invention is to provide a G force effect measuring arrangement which is highly immune to spoofing or results enhancement by a test subject.

Another object of the invention is to provide a G force effect sensing system which incorporates requirements for visual and psychomotor performance by the test subject.

Another object of the invention is to provide an improved acceleration G force sensing apparatus of the pursuit display type.

Another object of the invention is to provide an acceleration G force measurement system which is reliable and low in cost.

Another object of the invention is to provide a G force response measuring apparatus which includes a first array of visual stimuli elements dispersed around the peripheral view of a test subject, means for energizing the first array elements according to a first pattern of position and time, a second array of visual stimuli elements also dispersed around the peripheral view area of the test subject with each second array element being identified with a first array element, means controlled by the test subject for energizing the second array element in a second pattern which pursues the first pattern, and means for comparing the first and second patterns.

DETAILED DESCRIPTION

Figure 1:
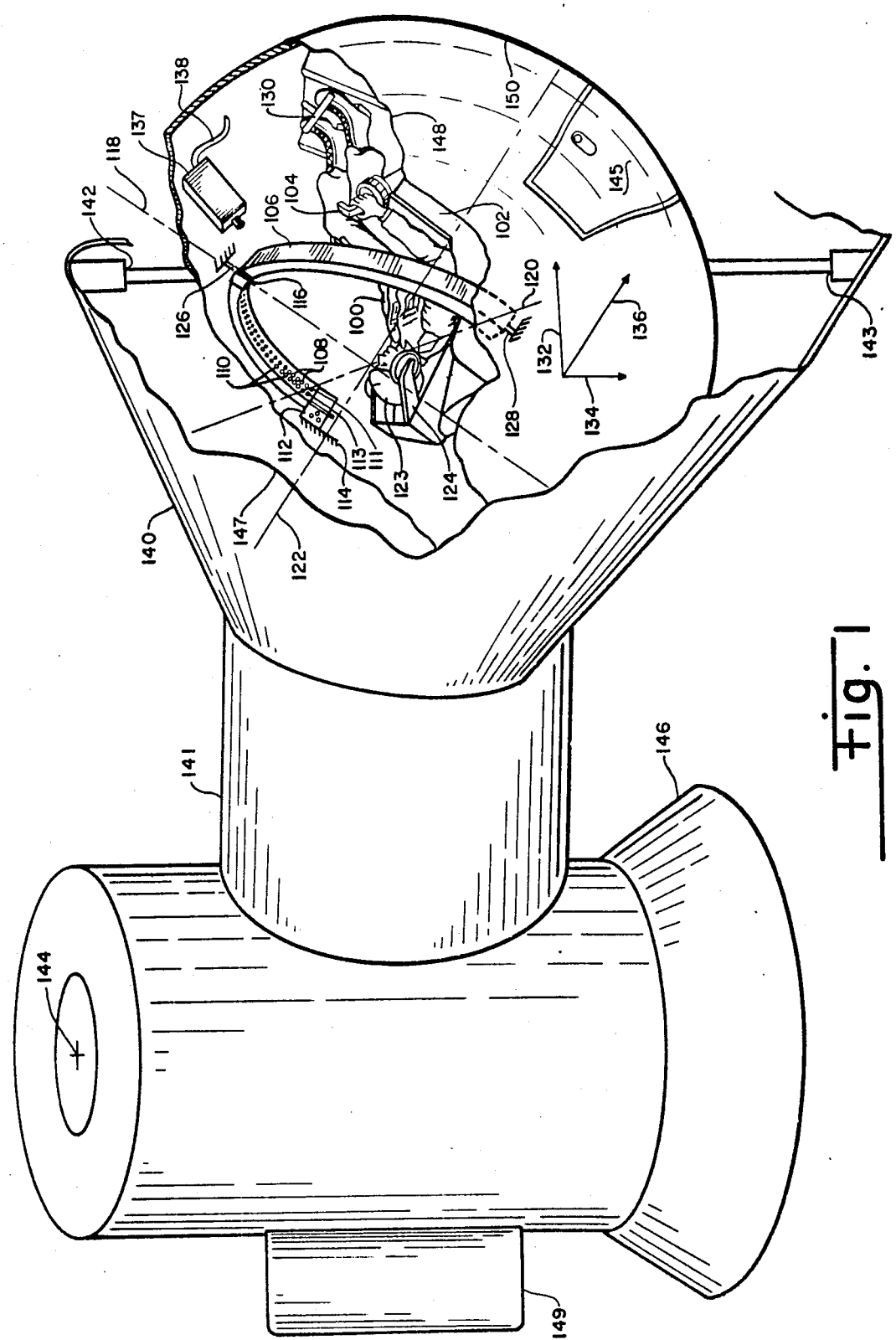
FIG. 1 is an overall view of a G force testing centrifuge which incorporates the random pattern tracking acceleration tolerance tester.

In FIG. 1 of the drawings, the acceleration tolerance testing apparatus of the present invention is shown incorporated into a centrifuge G force acceleration testing apparatus. This type of apparatus is frequently used for measuring the capability of a human to withstand and function under exposure to the acceleration forces encountered in a modern aircraft or spacecraft. The FIG. 1 centrifuge apparatus includes a spherical gondola 150 which is mounted in a yoke member 140 at the end of a radius arm 141. The arm 141 in turn is arranged to rotate about an axis 144 under the influence of electric motors or other prime moving apparatus contained within a mounting base 146. The yoke 140 is shown cut away at 147 in order that details of the spherical gondola 150 including the gondola cutaway portion indicated at 148 by visible. The centrifuge includes gondola mounting apparatus indicated generally at 142 and 143, by which the gondola 150 is movable in several degrees of freedom in order that the orientation of the test subject 100 be controlla be and in order that combinations of accelerating force, spin, roll and pitch be possible. The centrifuge may also include a counterweight 149 which frequently is embodied in the form of motors, slip ring assemblies and other mechanisms needed in connection with positioning and moving the test gondola 150. The FIG. 1 apparatus is shown approximately to size with respect to the size of the test subject 100. A centrifuge of this type is frequently arranged to achieve acceleration forces as large as 15 times the force of gravity (15 Gs), and is usually capable of relatively high rates of acceleration onset or decrease. These testing conditions are usually generated by electric motors of several hundred horsepower, rotating flywheels and other prime mover apparatus.

The spherical gondola 150 in FIG. 1 is shown oriented approximately in the direction providing maximum positive Z-axis acceleration force, indicated by the vector 136, to the test subject 100. The vector 136 is shown to be the resultant or summation of an acceleration force vector 132 and a gravity vector 134. Arrangements wherein the test subject 100 is positioned to receive maximum acceleration force along the X- or Y-axes, which are indicated at 118 and 120 in FIG. 1, are also frequently employed in order to simulate the effects experienced by present-day crew members during aircraft takeoff, landing, or rapid turning maneuvers. The gondola 150 is usually equipped with a test subject seating arrangement 102, head restraint apparatus 124, a helmet 123, feet and leg restraint apparatus as generally indicated at 130, an exit and entrance door 145, a television camera 137 and a joystick control 104. Signals from the TV camera 137 are transmitted by way of a cable 138 and slip rings to a monitoring console which is not shown. Other slip rings are used to carry electrical energy and test signals such as blood pressure and vital signs information concerning the test subject 100 to the monitoring console area; these slip rings also communicate electrical signals for energizing the light bar 106 and the joystick control 104.

Close attention to the physical well-being of the test subject 100 is required during use of the FIG. 1 apparatus. A television camera 137, open microphone communications and vital signs monitoring are of course essential portions of this close attention. An important additional part of this attention involves placing the test subject in a closed-loop or feedback visual and psychomotor monitoring system by way of the joystick control 104 and the light bar 106. The visual and psychomotor ability of the test subject are, as indicated above, particularly sensitive indicators of acceleration endurance limits and are sufficiently early in indicating ability to prevent the onset of hazardous conditions.

In the past, there has been a notable tendency for test subjects to incorporate an element of bravado in their response to light bar sensing arrangements which preceded the FIG. 1 apparatus. This response both degrades the usefulness of the test data and also introduces an undesirable element of hazard in testing of the FIG. 1 type. In these past examples, predictability of the pattern displayed by the light bar 106 was one factor which allowed the test subject to "fudge", or artificially respond to the light stimulus events.

The light bar 106 in the acceleration tolerance tester apparatus is mounted by a hinge 112 which connects to some fixed portion of the gondola 150 indicated at 114 in order that the light bar 106 can be easily moved up and away from the test subject 100 to facilitate entrance and exit of the test subject 100. This hinged mounting arrangement includes the detachable elements 126 and 128 located along the light bar 106 for additional support and convenient detachment.

As indicated by the two arrays of visual stimulus elements 111 and 113 in the light bar 106, the present invention contemplates the use of a double array of stimulus elements in order to achieve a more accurate indication of the test subject's capability during a FIG. 1 apparatus test. The visual stimulus elements 108 and 110 in the arrays 111 and 113 are preferably light emitting diodes (LEDs) of two different colors, for example, the lower row of elements in the array 111, element 108 etc., may be red light emitting diodes, while the upper row of elements, element 110 etc., may be green light emitting diodes. Although light emitting diodes are preferred as embodiments of the visual stimulus elements, other visual stimulus element arrangements, including but not limited to, incandescent lamps, electromechanical annucator devices, mechanically movable cursor members, and light projection arrangements, which might for example project images on the interior surface of the gondola 150 and dispense with the light bar 106, are within contemplation of the invention. The term "visual stimulus element" is therefore intended to be generic to a variety of test subject communicating arrangements which may be conceived for FIG. 1 type apparatus.

It should also be understood that the illustrated vertical alignment of the visual stimulus elements 108 and 110 is but one possible arrangement for elements which are identified with each other, alternate arrangements including side-by-side horizontal mounting, the use of concentric light emitters, mounting of the stimulus elements on the top and bottom surfaces of the light bar 106, and other relationships between the stimulus elements are also within contemplation of the invention.

In the present invention it is contemplated that the uppermost array of visual stimulus elements, as typified by the element 110, will be energized in some unpredictable or pseudorandom manner from a source of the type described below and that the test subject 100 will be instructed to manipulate the joystick 104 in order that the visual stimulus elements in the lower array, as typified by the element 108, track or follow this unpredictable upper array pattern. In the preferred embodiment, for example, a pattern involving excitation of two symetrically located light emitting diodes in the upper array of the light bar 106 and a movement of this symmetric excitation peripherally around LEDs in the light bar upper array is to be tracked or duplicated by a lower array pattern of two illuminated light emitting diodes positioned by the test subject's joystick 104.

In addition to the described two arrays of colored light emitting diodes or other visual stimulus elements, the FIG. 1 apparatus contemplates the presence of two third color visual stimulus elements such as two white lights at the center 116 of the light bar 106. These center located contrasting color stimulus elements provide a fixation point for the test subject 100 that has been found useful in helping a subject maintain orientation and in providing a reference for peripheral vision events occurring in the lower and upper arrays 111 and 113. Preferably the array center stimulus elements when embodied as light sources are arranged to be constantly illuminated and therefore may be comprised of incandescent lamps driven from any convenient energy source.

The number of elements to be included in each of the lower and upper arrays 111 and 113 is selectable between the endpoints of having so few elements as to provide inaccurate peripheral vision measurement and having too many elements resulting in unneeded complexity and test subject confusion. Arrays of sixty elements in each 90-degree quadrant of the light bar 106 have been found a satisfactory compromise between these endpoints. According to this arrangement, therefore, adjacent array elements are separated by one and one-half degrees of arc originating at the test subject's eyes. This one and one-half degree arcuate spacing of the array elements was also recommended in the above-cited U.S. Navy patent, U.S. Pat. No. 4,421,393. The disclosure of this Navy patent is hereby incorporated by reference into the present specification.

The above-indicated arrangement wherein the test subject responds to a random pattern of excitation in the upper light array 113 in FIG. 1 by maneuvering the joystick 104 and producing a similar movement pattern, or tracking, in the lower array 111 is identified as a special case of a pursuit display, as contrasted with a compensatory display. Compensatory displays are characterized by displaying only the error or difference between the forcing function signal and the response signal, while a pursuit display contains an indication of both the target and the response signals in separate display arrays. The U.S. Navy Cohen apparatus discussed above is, of course, a compensatory display, since only the difference between the target and joystick signals is displayed. A pursuit display provides more information to the test subject and those who monitor his response. Pursuit displays also add cognitive information to the man-machine system, that is, perception, recognition, and awareness are required of the test subject during G stress phases of an experiment by this form of display. The tracking performance which occurs from human subjects using a compensatory and a pursuit display is substantially different and is described in the textbook *Man-Machine Systems,* which is incorporated herein below. Since much of the response used in flying an aircraft or driving an automobile relate to pursuit rather than compensatory tracking, this form of display offers some realism advantage to a test environment.

Figure 2:
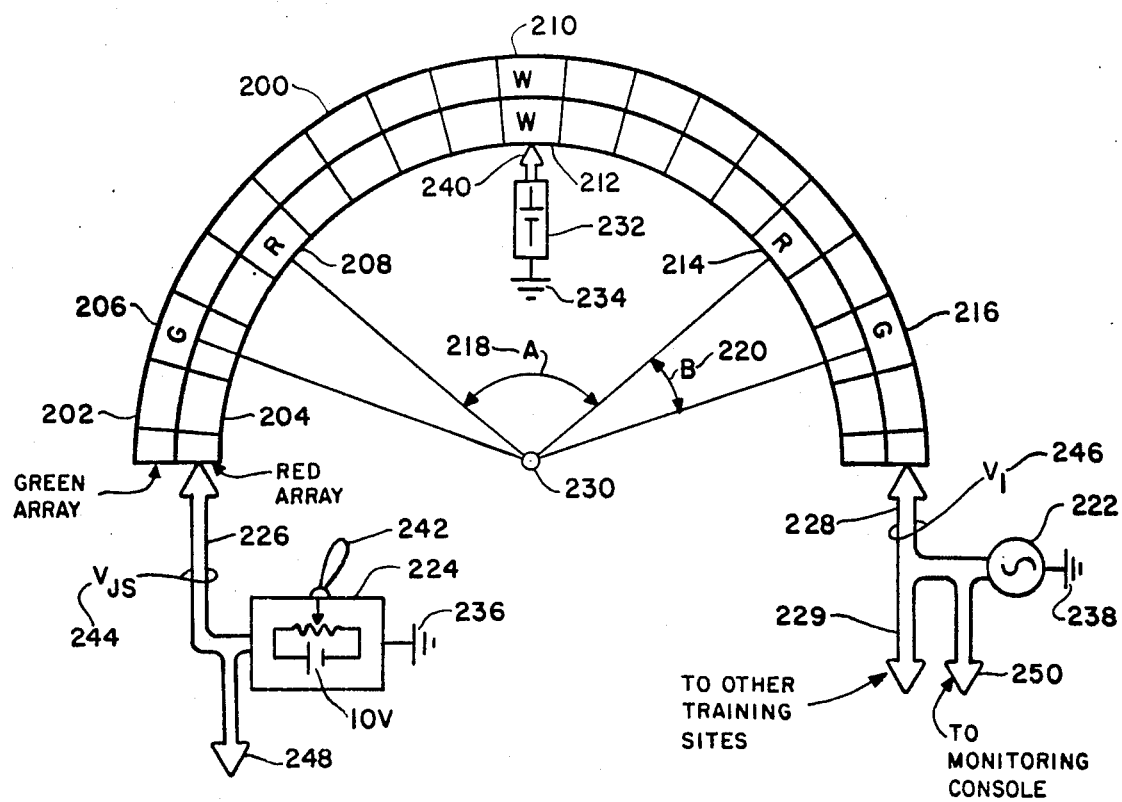
FIG. 2 is a functional diagram of the random pattern acceleration tolerances tester apparatus.

In FIG. 2 of the drawings there is shown a conceptual arrangement for energizing the light bar 106, including the arrays 111 and 113 in FIG. 1. The FIG. 2 diagram includes only a representative number of visual stimulus elements 202, it being understood that the sixty elements per 90-degree quadrant, or one and one-half degree arcuate spacing is preferred in a practical embodiment of the invention. In FIG. 2 the complete light bar assembly is indicated at 200 and illuminated LED or actuated visual stimulus elements in this assembly are indicated by the letters G and R at 206, 208, 214, and 216; the LEDs 208 and 214 are in the lower red array which is controlled by the test subject's joystick 242 and the LEDs 206 and 216 are in the upper green array which is controlled by the random signal source 222. The array center white lights are indicated at 210 and 212 in FIG. 2. A source of energy such as a battery 232 is indicated at 240 and 234 as being connected to the white lights. The connections 228 and 238 in FIG. 2 indicate connection of the random signal source 222 to the upper green array elements while connections 226 and 236 indicate connection of the test subject's joystick control 242 and its associated potentiometer(s) 224 to the lower red array.

At 218 and 220 in FIG. 2 are indicated the visual field angle, A, and an error angle, B, relating to a test subject viewing point 230. The visual field angle 218 for a normal person is on the order of 216 degrees, that is, a normal person has been found to have far field peripheral vision which extends slightly behind a hypothetical straight line extending across the front of his eyes. By way of example, a G force test subject is found to incur peripheral vision loss or peripheral light loss (PLL) under the influence of G force acceleration which reduces this 216 degree visual field to 50 degrees or less. PLL is arbitrarily defined as a condition existing when the test subject's central visual angle is less than 50 degrees.

For some positionings of a test subject with respect to the axis of rotation 144 in FIG. 1, the loss of peripheral vision is asymmetric in nature, that is, the peripheral vision in one eye may be diminished more than that of the other eye; this occurs most notably when the test subject is positioned to receive acceleration G force along the Y-axis 120 in FIG. 1. The contemplated symmetric excitation of the LEDs around the array center white lights, as indicated in FIG. 2 of the drawings allows a test subject to recognize a report such asymmetric visual capability.

The error angle 220, B in FIG. 2 may arise from a transient condition wherein the test subject has not yet had sufficient time to bring the joystick controlled red lower array LEDs into conformance with a newly occurring green upper array condition, such transient errors frequently persist for about 200 milliseconds and are ultimately corrected by the test subject. Angular errors 220 may arise from a more permanent loss of ability by the test subject and are to be thusly considered in scoring or evaluating the test subject's tolerance of the stress phase. For scoring purposes a root means square computation of the error angle B, 220, has been found useful. Such computation can be achieved through use of the relationship.

$$e_{RMS} = 1/N \sum_{i=1}^{N} e_i^2 \cdot t_i^{\frac{1}{2}}$$

where $e_t$ is the error signal angle, N is the number of samples of $e_t$ during the time period of interest and $e_{RMS}$ is the computed value of error angle B, 220 weighted for time. The time weighted error angle is usable for comparison scoring purposes. Signals for use in the monitoring console area and in performing the scoring computations are provided at 248 and 250 in FIG. 2.

Figures 3, 4:
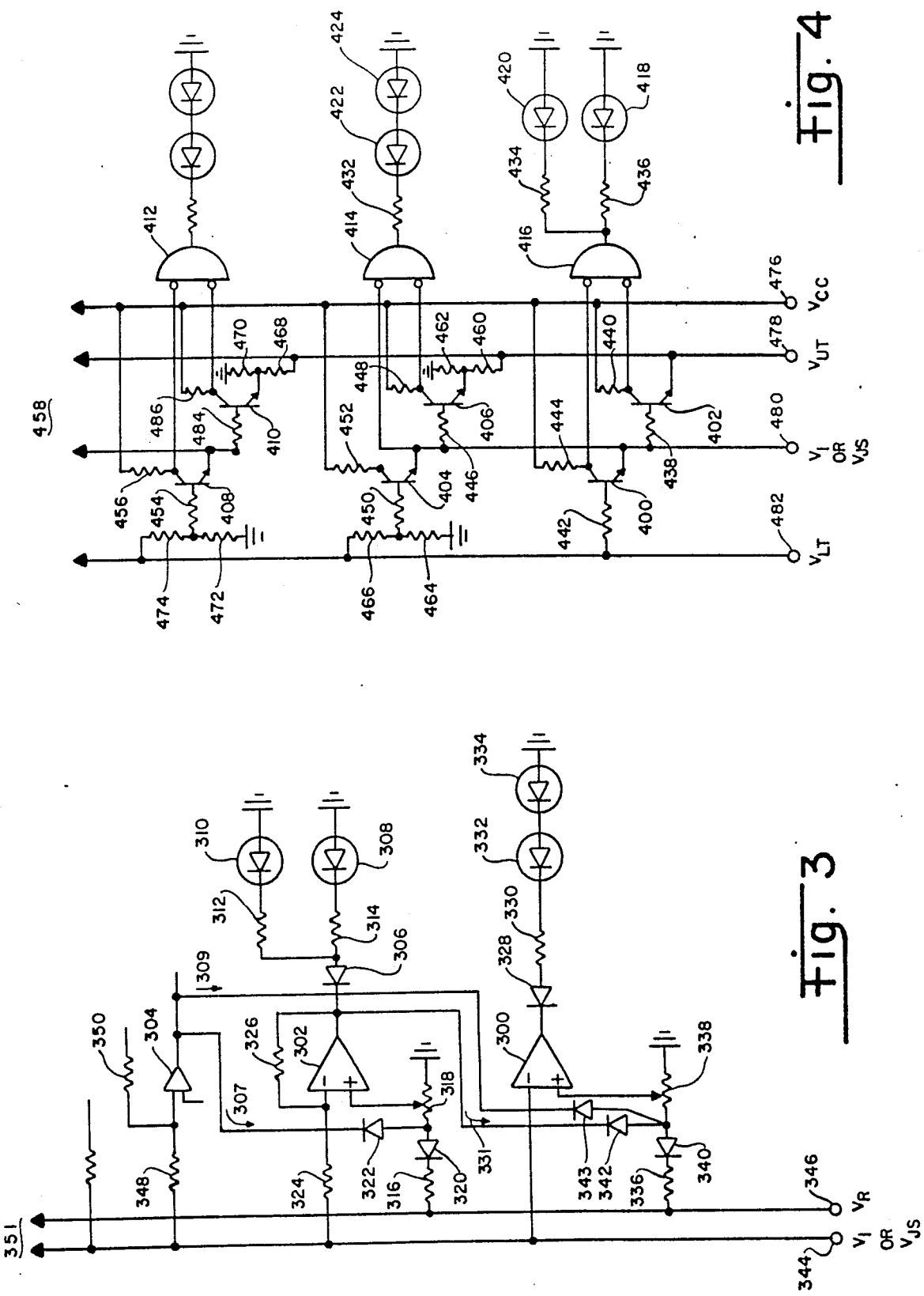
FIG. 3 is an electrical schematic diagram describing one possible circuit for energizing light emitting diode visual stimulus elements driven by a joystick control or a random signal source.
FIG. 4 is an electrical schematic diagram showing another possible circuit for energizing light emitting diode visual stimulus elements driven by a joystick control or a random signal source.

Several circuit arrangements are feasible for achieving the desired operation of the preferred LED elements in the FIG. 2 apparatus. One portion of these circuit arrangements includes the simultaneous excitation of symmetrically located LED elements and can be conveniently provided by connecting symmetrically located LED elements in electrical series or alternately in electrical parallel using of course current limiting resistors for each LED element or element pair as shown in FIG. 3 of the drawings and described below.

A plurality of possible embodiments for the random signal source 222 are feasible. One such embodiment, for example, might employ a random access memory (RAM) loaded with a table of appropriate numerical values with either the memory contents or the memory accessing being random in nature. It should be noted with respect to the random signal source 222 that a pure random excitation of LED elements would provide some excitation periods and transition periods which would be undesirably short or conversely, undesirably long in duration; the desirable algorithm for the random signal source 222 is therefore of a pseudo-random nature wherein the transitions are of a human trackable nature.

Another embodiment of the random source 222, one that is in fact preferred, involves the use of a sum of sines algorithm. In order for such a sinusoidal-based forcing or driving function to appear random to the human subject, the preferred LED driving function is composed of a minimum of five sine waves of different frequencies and is arranged to have zero mean over the duration of an experiment stress phase (each sine wave repeats itself an integral number of periods over the duration of the stress phase) with each sine wave having a differing initial phase angle. In the textbook *Man-Machine Systems* by T. B. Sheridan and W. R. Ferrell, which is hereby incorporated herein by reference, it is shown empirically that if five or more different sine waves are added together in this manner, then a human subject is not able to predict the periodic behavior of the resulting signal. In general, therefore, the length of the G force test run in seconds may be made equal to two periods of the lowest frequency sine wave, called the fundamental, to be employed. This fundamental frequency would be 1/10 Hz for a 20 second G force stress period, for example. The five component sine wave frequencies may be then made prime number multiples of this fundamental frequency in order to achieve the condition that no two frequencies can ever be integer multiples of each other.

The sum of sines LED forcing function algorithm then operates in accordance with the mathematical equation.

$$v_1 = a_o + \sum_{i=1}^{n} |a_i \mathrm{Sin}(w_i t + \phi_i)|$$

In this equation $V_1$ is the output signal which is decoded or threshold detected to determine the on-time of green array LEDs, for example. The term $a_o$ in the $V_1$ equation represents a DC voltage chosen to maintain a pair of green LED elements in the "on" condition to cover a field of view of at least 50° of the test subject. The summation from $i=1$ to $i=n$ indicates the presence of several sine waves, five sine waves being a preferred arrangement. The term $a_i$ is a constant determining the relative peak amplitudes of the selected component sine waves and their amplitude with respect to the component $a_o$, the $a_i$ term may be different for each of the component sine waves. The term $W_i t$ in the $V_1$ equation identifies the frequency of each sine wave component and the term $\phi_i$ determines the relative phasing of the individual sine wave components.

According to this visual stimulus energization arrangement, the green lights oscillate in the periphery of the test subject's eye and the subject must track the border of these lights using the pair of red lights to align with the green lights. The voltage $a_o$ in the above equation determines the peripheral light loss angle and the dark to green oscillations occur about this voltage value. If the subject cannot see in the periphery, he also, of course, is incapable of tracking the green lights. Since the subject is instructed to stare straight ahead, he cannot claim to see in his periphery if he does not cause the pair of red lights to follow the pair of oscillating green lights. Thus, the invention provides a true empirical measure of whether a test subject can actually see in the periphery rather than relying on subjective comments which may be biased or in error.

A preferred arrangement for generating the sum of sines LED driving function involves the use of a digital computer which is programmed in accordance with the above-described concepts. Such a computer can be the type PDP-11 manufactured by Digital Equipment Corporation (DEC) of Boston, Mass. A listing of a FORTRAN IV program capable of generating the sum of sines driving function is shown at the end of this specification. Other program arrangements and other driving function arrangements can, of course, be fabricated within the contemplation of the invention.

Figure 5:
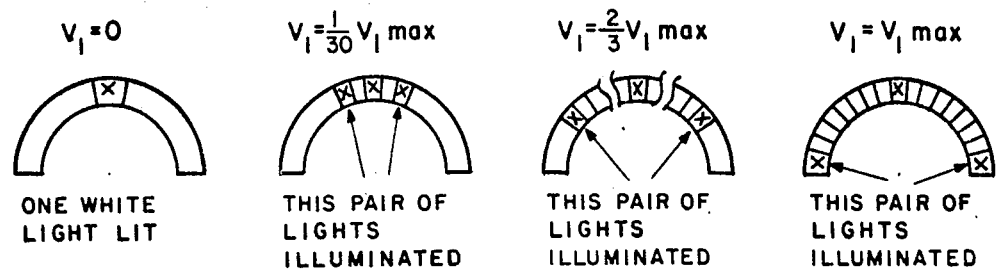
FIG. 5 is a diagrammatic representation of a random pattern apparatus illustrating a position signal response therein.

The desired arrangement for causing the green lights to go on in relation to the magnitude of the voltage $V_1$ is believed to be understood, but will now be briefly described. If $V_1$ is at its maximum voltage, the furthest pair of LED lights in the periphery are desirably in the "on" condition. If $V_1 = 0$, only the center white light remains on. For a voltage between $V_1$ max and 0 volts, the pair of lights that go on are symmetrical about the center white light and their distance from the center is proportional to the voltage $V_1$. For example, in FIG. 5, if $V_1 = (1/60) V_{max}$, and $V_{max} = 10$ volts, the pair of green lights illuminated is based on the number $V_1/V_{max} (60) \approx 1$, or the first light on each side of the center light is to be energized. If $V_1 = (\frac{2}{3}) V_{max}$, then the pair of green lights illuminated is based on $\frac{2}{3} (60) =$ the fortieth lights. Thus, the center 19 lights are not illuminated, but the pair of lights a distance 20 from the center are illuminated along with the center reference light. The manner in which the red lights are driven from the voltage developed by the test subject manipulated joystick follows in a similar relationship as for the green lights. When the joystick is in the zero position, the potentiometer arm voltage is zero volts and only the reference light in the center is lit. When the maximum voltage (e.g., 10 volts) is used from the joystick potentiometer, the outside pair of lights and the reference light will be energized. As in the random excited green array, the distance of the energized red array pair from the center is proportional to the voltage obtained from the potentiometer arm.

Electronic circuitry capable of converting the $V_1$ voltage signal provided by either the sum of sines algorithm or the random number algorithm or the $V_{JS}$ joystick potentiometer signal into signals capable of energizing light emitting diode (LED) elements is known in the electronic circuit art. Essentially such circuitry involves a voltage discriminating arrangement wherein one symmetrically located pair of LED elements is illuminated for each value of the $V_1$ signal indicated at 246 in FIG. 2. In similar fashion such voltage discriminating circuitry can also be used to illuminate one symmetrically located pair of LED elements in response to each possible value of the joystick output signal $V_{JS}$, 244 in FIG. 2. Generally, voltage discriminating circuitry of this type may be fabricated around an operational amplifier threshold sensing circuit or around a digital logic circuit arrangement, examples of each of these circuits are shown in FIGS. 3 and 4 of the drawings.

The FIG. 4 voltage discriminating circuit employs a number of bipolar NPN transistors 400-410 for sensing the relative polarities between the $V_1$ or $V_{JS}$ signals and a pair of reference signals $V_{LT}$ and $V_{UT}$, these signals being received on busses 482, 480 and 478. The signals on these busses may be obtained from appropriate sources such as the joystick potentiometer and the sum of sines generator 224 and 222 in FIG. 2 in the case of the $V_1$ or $V_{JS}$ signal and from adjustable potentiometers for the $V_{LT}$ and $V_{UT}$ signals. These bus signals may also be increased as to load driving ability through the use of suitable buffering amplifiers.

Operation of the FIG. 4 circuit is based on the concept that conduction in the transistor 402, for example, occurs when the $V_1$ signal is more positive than the $V_{UT}$ signal and similarly, conduction occurs in the transistor 400 when the $V_1$ signal is less positive than the $V_{LT}$ signal. Conduction in the transistors 400 and 402 causes their collector output voltages to be in the low level condition and these low level signals are received at a NOR gate 416 and provide a high level signal output therefrom to energize the two light emitting diodes 418 and 420. If either of the transistors 400 and 402 depart from the conducting condition because of a change in the relative polarity of the $V_1$ signal with respect to the $V_{LT}$ or $V_{UT}$ signals, the output of the NOR gate 416 will change to the low level condition and the two light emitting diodes 418 and 420 will be extinguished.

Current level and light intensity in the LED elements is determined by the value of the resistors 434 and 436 and the output signal level of the NOR gate 416. The voltage divider resistor elements 460-474 in FIG. 4 provide a means for adjusting the value of the reference signal period to the successive pairs of transistors 404 and 406, 408 and 410 in order that each of the LED pairs 418 and 420, 422 and 424, and 426 and 428 be responsive to differing levels of the $V_1$ or $V_{JS}$ signals.

As indicated by the parallel connection of the LED elements 418 and 420 and the series connection of the LED elements 422 and 424 either of these connection arrangements is feasible for two symmetrically placed LEDs in the light bar assembly. The series resistors 438, 442, 446, 450, 454 and 484 control the base current in the transistors 400-410 in a manner known in the art. The collectors of these transistors are connected to a collector voltage supply, which in the FIG. 4 circuit should be positive in polarity, by means of collector load resistors 440, 444, 448, 452, 456 and 486 as is also known in the art. Since the output signal from the transistors 400, 402 etc. during the transistor conduction interval will depend on the voltages existing on the busses 478 and 480 a relatively large value of $V_{CC}$ from the collector supply bus 476 is desirable and a correspondingly large input signal capability for the NOR gates 412-416 is desirable. As indicated at 458, the FIG. 4 apparatus contemplates the presence of additional circuits of the type shown, sixty such circuits are required in the preferred embodiment apparatus.

Another voltage discriminating circuit which avoids the above-described bus signal variations at the input of the NOR gates in FIG. 4 is shown in FIG. 3 of the drawings. The FIG. 3 circuit involves the use of operational-amplifier voltage-discriminating circuits of the type commonly available in integrated circuit form in the electronic art. The FIG. 3 circuit is based on sensing the transition of the buffered $V_1$ or $V_{JS}$ signals applied at bus 344, from a condition smaller than a reference signal $V_R$, to a condition larger than the reference signal $V_R$. The buffered $V_R$ reference signal is received on the bus 346 and is appropriately divided for each of the operational amplifiers 300-304 by the voltage dividers 336, 338 and 316, 318. The output of the operational amplifier 300 will, for example, approach the voltage of the positive supply rail for the amplifier (which is not shown in FIG. 3) so long as the signal at its negative input terminal is more negative than the signal at the positive input terminal. Once the $V_1$ signal increases in magnitude and becomes more positive than the $V_R$ signal, the output of the operational amplifier 300 will approach the negative supply rail, causing conduction in the diode 328 and the resistor 330 and illumination of the LEDs 332 and 334.

The reference signal on the bus 346 is shown to have a negative polarity in FIG. 3 in order to accommodate the polarity reversal occurring at the negative input of the operational amplifier 300. The use of such negative signals and negative or inverting amplifier input terminals and the corresponding polarity of the diodes 328, 332 and 334 is well known in the electronic art. The value of the reference signal applied to the positive terminal of the operational amplifier 300 and 302 is selected by adjusting the potentiometers 318 and 338, a precisely determined and slightly different value being contemplated for each of the 60 operational amplifiers in the preferred embodiment apparatus.

As the $V_1$ or $V_{JS}$ input signal on the bus 344 progresses in a more positive direction, successive ones of the operational amplifiers 300, 302 and 304 will be turned on, that is, will switch from the positive output to the negative output condition. The turning on of the amplifier 302 causes turn-off of the amplifier 300 by way of signal transmitted along the path 331 which adjusts the value of the reference signal supplied to the amplifier 300 by way of the gating diodes 342 and 340. The effective reference signal at each operational amplifier is the more negative of the signals received by way of the diodes 342, 343, and 340. In similar fashion, turn-on of the amplifier 304 accomplishes turn-off of amplifier 302 and maintenance of the turn-off condition in the amplifier 300 by way of signal coupled along the paths 307 and 309 and the diodes 322 and 343. The relative values of the resistors 316 and 318, 336 and 338 determines the initial turn-on point for each of the operational amplifiers 300 and 302.

The operating band or sensitivity of each of the operational amplifiers 300-304 in FIG. 3, that is, the band of input voltage values wherein the LEDs 308 and 310, for example, will remain in the energized condition can be adjusted with the negative feedback gain controlling resistor network 324 and 326 in a manner known in the operational amplifier art. The use of such gain determining resistor elements may not be necessary, depending on the parameters of an individual embodiment of the circuit; this is indicated by omission of gain determining resistors for the operational amplifier 300 and inclusion of resistor 348 and 350 for the operational amplifier 304.

As was indicated in FIG. 4, either a series or parallel connection of the symmetrically located LED elements is feasible and is indicated by the series connection of LEDs 332 and 334 and parallel connection of the LEDs 308 and 310. Current limiting in each of these connection arrangements is provided by the resistors 312, 314 and 330. The diodes 306 and 328 serve to protect the LEDs from the large voltage present at the output of the operational amplifiers when these amplifiers are in the off state.

It should be understood that the system herein disclosed can be arranged to include a plurality of the light bar and joystick elements in separate locations in order to provide an off-line test subject training facility wherein the test subjects can be acclimated to the performance of the system and the stress phase tasks required of them. Off-line training of this type can also be advantageous in avoiding the errors which tend to occur when learning is accomplished in the stress phase of an experiment. In a parallel training arrangement it would of course be possible to operate several of the FIG. 1 and FIG. 2 light bar array assemblies from a single random signal source 222 merely by paralleling driver circuits which are exicted by a single random signal source and also including plural white light elements operated from the battery 232 or an alternating current transformer or other energy source. The visual stimulus patterns in parallel operated display arrays would of course be identical. Such identical stimulus displays could also be used for competitive endeavors involved in a test subject training program. Off-line preliminary exposure could also be used for establishing a normal response time profile for test subjects outside the G force environment. The path 229 in FIG. 2 provides the signal needed for an off-line training facility.

Both the training capability and the centrifuge mounted light bar apparatus may also be useful in tests involving non-human participants such as primate, canine, or possibly rodent test subjects—after a sufficient degree of training. The pursuit display of the present invention is believed to be more comprehendable by such a non-human subject than would be the compensatory display used in the prior art. The relatively low cost of the entire tracking acceleration tolerance tester and especially of off-line training stations justifies the use of multiple stations.

Concerning the selection of visual stimulus element colors, red and green are standard colors for LEDs and therefore are readily available for use in the FIG. 1 and 2 apparatus. Studies have shown, however, that in the periphery of the eye, where the retinal rods rather than the cones are the predominant visual receptor, short wavelength light (blue, green) are more sensitively perceived as compared to long wavelength light (red) under G stress. It is therefore possible that green or white light is to be preferred for peripheral viewing, and that red light is less desirable in this use. In the present invention visual stimulus elements, however, if the lights were made to be all the same color, such as all green or all white, then the test subject could confuse the target signal with the response signal and have a tendency to make joystick movement in the wrong direction (i.e., control reversal could occur). The preferred use of LED visual stimulus elements of red and green colors is therefore a practical and desirable compromise and is not a limitation of the invention; other colors and other forms of stimulus elements are easily arranged.

In the described embodiment of the invention the test subject's joystick 104 and 242 in FIGS. 1 and 2 provide actual position control of the illuminated red LED array element, that is, the illuminated LED element is directly responsive to the position of the joystick. An alternate embodiment of the invention could be achieved by arranging the joystick to provide position incrementing of the illuminated red LED array element rather than actual position control. In such an embodiment the test subject would maintain the joystick in a neutral or home position so long as the illuminated red and green LEDs are aligned and move the joystick in an appropriate direction when alignment correction is needed. An embodiment of this type would, of course, somewhat approach the concept of the compensatory system but would retain the pursuit characteristic of the display. Position incrementing may be achieved using some form of electronic memory such as a position voltage stored on a capacitor; such a circuit may be fabricated using an operational amplifier connected into an integrating configuration with the required capacitor connected between the output and negative input amplifier terminals.

It should be realized that other pattern arrangements may be employed with the invention, for example, a pattern wherein the array elements operate in thermometer fashion, e.g., commencing at the outer periphery and remaining in the on condition once excited up to a transition point which moves about randomly. Other excitation patterns involving a greater number of LED elements excited at a given time may also be employed.

The described apparatus provides several notable advantages over prior art sensing arrangements for use with G force testing, these include the reduction or elimination of the tendency for test subjects to enhance or bravado their performance in a G stress environment, improved feedback psychology to the test subject through the use of pursuit display double arrays of visual stimulus elements, reliable operation with low fabrication and operating costs, a selection of visual stimulus colors which can be used to avoid the retina bleaching or local adaptation described in the above referenced prior art, and the reduction or elimination of test subject prediction of light patterns.

While the apparatus and method herein described constitute a preferred embodiment of the invention, it is to be understood that the invention is not limited to this precise form of apparatus or method, and that changes may be made therein without departing from the scope of the invention, which is defined in the appended claims.

| SUM OF SINES COMPUTER PROGRAM |
| --- |
| PROGRAM MAIN (INPUT, OUTPUT, TAPE6=INPUT, TAPES5=OUTPUT) |
| DIMENSION A(5,101), PHI(5), W(5), B(5), TIME(101) |
| ATOTAL(102) |
| C  SET INITIAL CONDITIONS ON EACH SINE WAVE |
|     DØ 1 I=1,5 |
| 1  PHI(I)=RAND(I) |
| C  RAND(I) IS THE SUBROUTINE FOR GENERATING RANDOM NUMBERS |
| C  NOW SET THE FIVE FREQUENCIES |
|     WZ=2.357 |
|     W(1)=2*WZ |
|     W(2)=3.*WZ |
|     W(3)=5.*WZ |
|     W(4)=7.*WZ |
|     W(5)=11.*WZ |
| C  NOW SET THE MAGNITUDES (AMPLITUDES) OF EACH SINE WAVE |
|     B(1)=1.1 |
|     B(2)=.8 |
|     B(3)=.6 |
|     B(4)=.4 |
|     B(5)=.3 |
| C  NOW STORE THE TIME FUNCTION |
|     TF=5.0 |
|     DØ 2 I=1, 101 |
| 2  TIME(I)=(I=1)*TF/100. |
| C  NOW GENERATE THE SINE WAVE |
|     ATOTAL(1)=0. |
|     DØ 3 J=1, 101 |
|     DØ 4 I=1, 5 |
|     A(I,J)=B(I)*SIN(W(I)*TIME(J)+PHI(I)) |
| 4  ATOTAL(J)=ATOTAL(J)+A(I,J) |
|     IF (I=5) 7, 7, 6 |
| 7  ATOTAL (J+1)=0 |
| 6  CONTINUE |
| 3  CONTINUE |
|     END |

We claim:

1. G force response measuring apparatus comprising the combination of:

a first array of visual stimulus elements dispersed around the preripheral view area of a test subject;

means for energizing said first array elements to a visual stimulating state thereof according to a first random time pattern;

a second array of visual stimulus elements dispersed around the peripheral view area of said test subject, each second array element being located adjacent a first array element;

means for energizing said second array elements to a visual stimulating state thereof in a second test subject controlled pattern tracking said first pattern to the best degree attainable by said test subject; and means for determining the difference error between said first and second patterns.

2. The apparatus of claim 1 wherein said means for determining the difference error between said first and second patterns is responsive to both first to second pattern displacement differences and first to second pattern time delay differences.

3. The apparatus of claim 1 wherein said first and second patterns comprise a moving transition between energized and nonenergized stimulus elements.

4. The apparatus of claim 3 wherein each said first and second patterns comprise energization of a single array element at one time.

5. The apparatus of claim 4 wherein said visual stimuli array elements are comprised of light emitting diodes.

6. The apparatus of claim 5 wherein said first array and second array elements emit light of two different colors.

7. The apparatus of claim 6 wherein said two different colors are red and green.

8. The apparatus of claim 7 further including an arraycenter visual stimulus element of contrasting color and full time energization.

9. The apparatus of claim 8 wherein said light emitting diodes are located at one and one-half degree arcuate intervals around the peripheral view of said test subject and wherein said contrasting color element comprises a white light element located in the array center position of each array.

10. The apparatus of claim 1 further including scoring means responsive to differences between said first and second patterns.

11. The apparatus of claim 10 wherein said scoring means includes a root means square evaluation of time and amplitude differences between said first and second patterns.

12. The apparatus of claim 1 wherein said first pattern includes a sum of sines pseudo-random algorithm.

13. The apparatus of claim 12 wherein said sum of sines algorithm includes at least five non-integral related sine waves.

14. The apparatus of claim 1 wherein said test subject is a human.

15. The apparatus of claim 14 wherein said visual stimulus elements are located in a semicircular, movably mounted light bar extending around the peripheral view of said human test subject.

16. The apparatus of claim 12 wherein said means controlled by said test subject includes a joystick control element.

17. The apparatus of claim 1 wherein said means for determining difference error includes a chart recorder capable of simultaneous recording of first and second pattern events.

18. A method of determining the endurance limit of a human test subject to acceleration G forces comprising the steps of:

moving a first visual stimulus randomly about the peripheral extending view field of said test subject;

tracking the position of said first visual stimulus with a test subject-controlled simultaneously observed second visual stimulus that is position movable into and out of coincidence with said first visual stimulus in response to said test subject control; and sensing the loss of stimulus tracking ability in the test subject peripheral view field with G force exposure.

19. Apparatus for measuring the G force response of a test subject comprising:

first visual stimulus means movable in location around the peripheral view field of said test subject;

means for moving said first visual stimulus means randomly about said peripheral view field;

second visual stimulus means movable in location around said peripheral view field in response to control by said test subject for tracking the position of said first visual stimulus means in response to control by said test subject; and means for sensing the G force-induced loss of stimuli tracking capability in far peripheral view field areas of said test subject.

20. The apparatus of claim 19 wherein said means for moving randomly includes a sum of sines movement algorithm.

21. The apparatus of claim 20 wherein said visual stimuli comprise light emitting diode elements.

22. The apparatus of claim 21 further including additional first and second stimulus light emitting diode element arrays located remote said first and second visual stimulus means.

23. The apparatus of claim 22 further including hinged mounting means for removably positioning said visual stimulus means with respect to a test subject.

* * * * *

UNITED STATES PATENT AND TRADEMARK OFFICE
CERTIFICATE OF CORRECTION

PATENT NO. : 4,619,506

DATED : October 28, 1986

INVENTOR(S) : Daniel W. Repperger et al

It is certified that error appears in the above-identified patent and that said Letters Patent is hereby corrected as shown below:

Column 1, line 7, "U.S." should read --United States--.

Column 3, line 18, "n" should read --in--.

Column 4, line 58, "controlla be" should read --controllable--.

Column 5, line 55, "114" should read --104--.

Column 8, line 14, "a" (second occurrence) should read --and--

Signed and Sealed this

Thirty-first Day of March, 1987

Attest:

DONALD J. QUIGG

Attesting Officer

Commissioner of Patents and Trademarks